(12) United States Patent
Keller et al.

(10) Patent No.: US 9,198,859 B2
(45) Date of Patent: Dec. 1, 2015

(54) CONCENTRATED MAST CELL STABILIZING PHARMACEUTICAL FORMULATIONS

(75) Inventors: Manfred Keller, München (DE); Roman Egle, München (DE)

(73) Assignee: PARI Pharma GMBH, Starnberg (DE)

( * ) Notice: Subject to any disclaimer, the term of this patent is extended or adjusted under 35 U.S.C. 154(b) by 671 days.

(21) Appl. No.: 13/291,488

(22) Filed: Nov. 8, 2011

(65) Prior Publication Data

US 2012/0118991 A1    May 17, 2012

Related U.S. Application Data

(63) Continuation-in-part of application No. PCT/EP2010/056197, filed on May 6, 2010.

(30) Foreign Application Priority Data

May 8, 2009  (EP) .................................. 09006294

(51) Int. Cl.
| | |
|---|---|
| *B05B 15/00* | (2006.01) |
| *A61P 11/06* | (2006.01) |
| *A61P 11/00* | (2006.01) |
| *A61K 31/353* | (2006.01) |
| *A61K 9/08* | (2006.01) |
| *A61K 9/00* | (2006.01) |
| *A61K 47/02* | (2006.01) |
| *A61K 47/12* | (2006.01) |

(Continued)

(52) U.S. Cl.
CPC ............ *A61K 9/08* (2013.01); *A61K 9/0078* (2013.01); *A61K 47/02* (2013.01); *A61K 47/12* (2013.01); *A61K 47/183* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 2004/0045546 A1* | 3/2004 | Hirsh et al. ............... | 128/200.14 |
| 2007/0193577 A1* | 8/2007 | Keller ...................... | 128/200.14 |

(Continued)

FOREIGN PATENT DOCUMENTS

| | | |
|---|---|---|
| DE | 10 2005 038 619 A1 | 2/2007 |
| DE | 10 2007 056 462 A1 | 5/2009 |

(Continued)

OTHER PUBLICATIONS

M. Keller et al., "Importance of the Inhaler System and Relative Humidity on the Fine Particle Dose (FPD) of Disodium Cromoglycate (DSCG)", Respiratory Drug Delivery Europe 2007, pp. 307-310.

(Continued)

*Primary Examiner* — Bethany Barham
*Assistant Examiner* — Dominic Lazaro
(74) *Attorney, Agent, or Firm* — Mintz Levin Cohn Ferris Glovsky and Popeo, P.C.; Peter F. Corless; Christopher R. Cowles (57) ABSTRACT

Liquid aqueous pharmaceutical solutions, containing a mast cell stabilizing active agent for application to the upper and lower respiratory tract or in the eye are provided. The solutions comprise both a non-ionic and an ionic tonicity-adjusting excipient. They are particularly useful for the aerosol treatment of respiratory diseases such as asthma. Furthermore, methods for nebulization of these solutions and methods of packaging the solutions are provided.

18 Claims, 1 Drawing Sheet

(51) Int. Cl.
*A61K 47/18* (2006.01)
*A61K 47/26* (2006.01)

(56) References Cited

U.S. PATENT DOCUMENTS

2009/0137950 A1  5/2009  Loenner et al.
2009/0293868 A1  12/2009  Hetzer et al.

FOREIGN PATENT DOCUMENTS

| EP | 0 212 927 A1 | 3/1987 |
| EP | 0 274 590 A1 | 7/1988 |
| EP | 0 413 583 A2 | 2/1991 |
| EP | 0 587 264 A1 | 3/1994 |
| EP | 0 933 084 A1 | 8/1999 |
| EP | 2 030 644 A1 | 3/2009 |
| EP | 2030644 A1 * | 3/2009 |
| WO | 97/15284 A1 | 5/1997 |
| WO | 2007/090646 A1 | 8/2007 |
| WO | 2009/027095 A1 | 3/2009 |

OTHER PUBLICATIONS

Q. Hamid et al., "Respiratory pathophysiologic responses: Inflammation of small airways in asthma", J. Allergy Clin Immunol., 100(1), pp. 44-51 (1997).

K. Hashimoto et al., "DSCG Reduces RSV-Induced Illness in RSV-Infected Mice", Journal of Medical Virology, vol. 81, pp. 354-361 (2009).

K.I.P.J. Hidari et al., "In Vitro and in Vivo Inhibitory Effects of Disodium Cromoglycate on Influenza Virus Infection", Biol. Pharm. Bull., 27(6), pp. 825-830 (2004).

M. Keller et al., "Using Infant Deposition Models to Improve Inhaler System Design", Respiratory Drug Delivery, IX, 2004, pp. 221-232.

J.C. van der Wouden et al., "Inhaled sodium cromoglycate for asthma in children", The Cochrane Database of Systematic Reviews 2003, pp. 1-44.

M. Alexander et al., "Efficacy of an isotonic small droplet size nebulized DSCG on asthma contol in children", European Respiratory Society Conference 2008, Poster No. 3958.

A.A. Norris et al., "Cromolyn Sodium and Nedocromil Sodium", Allergy: Principles & Practices, edition 5, Chapter 47, Middleton et al., pp. 661-667 (1998).

W. Petersen et al., "Sodium cromoglycate as a replacement for inhaled corticosteroids in mild-to-moderate childhood asthma", Allergy, pp. 870-875 (1996).

M.T. Stevens et al., "Sodium cromoglicate: an ineffective drug or meta-analysis misused?", Pharmaceutical Statistics, vol. 6, pp. 123-137 (2007).

M.J.A. Tasche et al., "Inhaled disodium cromoglycate (DSCG) as maintenance therapy in children with asthma: a systematic review", Thorax, vol. 55, pp. 913-920 (2000).

M.K. Tulic et al., "Contribution of the Distal Lung to the Pathologic and Physiologic Changes in Asthma", Chest, vol. 123, pp. 348S-355S (2003).

J. Bousquet et al., "Asthma: From Bronchoconstriction to Airways Inflammation and Remodeling", Am. J. Respir. Crit. Care Med., 161(5), pp. 1720-1745 (2000).

G.A. Ferron et al., "Estimation of the Deposition of Aerosolized Drugs in the Human Respiratory Tract Due to Hygroscopic Growth", Journal of Aerosol Medicine, 2(3), pp. 271-284 (1989).

* cited by examiner

CONCENTRATED MAST CELL STABILIZING PHARMACEUTICAL FORMULATIONS

FIELD OF THE INVENTION

The invention relates to liquid aqueous pharmaceutical compositions comprising high concentrations of mast cell stabilizing agents, useful for aerosol and topical application. The invention also relates to methods for nebulizing these mast cell stabilizing compositions. The compositions are particularly useful for treatment and prevention of conditions affecting the respiratory tract or parts thereof, such as the upper respiratory tract, including the nose and sinonasal cavities, and the lower respiratory tract, including the bronchi and the lungs. In another aspect, the compositions are useful for application to the eye, ear or skin.

BACKGROUND OF THE INVENTION

Asthma is a major cause of morbidity and mortality in the world and is estimated to affect around 300 million people worldwide. It is estimated that an additional 100 million people will suffer from asthma in 2025. The increasing prevalence especially affects children. Currently, asthma is the death cause for 1 out of 250 deaths, which in many cases is due to insufficient treatment (www.ginasthma.com).

Although the exact cause of asthma is not fully understood, it is known to be characterised by inflammation of the airways and a decline in respiratory function. In asthma, a number of inflammatory cells, including eosinophiles and $CD4^+$ T-lymphocytes are thought to contribute to the pathogenesis of the disease. Further important features are the presence of airway wall remodelling, hyperplasia/hypertrophy of airway smooth muscle, increased collagen deposition beneath the basement membrane, increased mucus production, angiogenesis and alterations in extracellular matrix (Bousquet et al. Asthma—from bronchoconstriction to airways inflammation and remodeling. Am J Respir Crit Care Med 2000; 161(5):1720-1745). Furthermore, there are reports suggesting that severe viral infections in infants are a risk factor for airway hyperresponsiveness and bronchial asthma in later life (Hashimoto et al. DSCG Reduces RSV-Induced Illness in RSV-Infected Mice. J Med Virol 2009; 81:354-361).

Disodium cromoglycate (DSCG) is a safe and widely used drug for the prevention of bronchial asthma, allergic rhinitis and conjunctivitis attacks. It is recommended in current guidelines for treatment of asthma, such as the guidelines published by the Global Initiative for Asthma (GINA), as an alternative therapy for the standard recommended glucocorticosteroids, long-acting $\beta_2$-agonists, theophylline and leukotriene modifiers.

The first choice therapy recommended for long-term management of asthma in European, US and Japanese guidelines is inhalation of corticosteroids. Although these guidelines note that currently available inhaled corticosteroids are safer, they also warn that chronic use of inhaled corticosteroids initiated in childhood and continued through adulthood might have cumulative effects that increase the relative risk of certain conditions such as osteoporosis, cataract or glaucoma in later life. Due to these and other side effects, it is not always justifiable to use inhaled corticosteroids for treatment of mild asthma, especially in young children. In contrast, DSCG has a safety profile encompassing more than 35 years of clinical use. The majority of controlled, direct comparisons of DSCG and inhaled corticosteroids in children with mild-to-moderate asthma showed comparable efficacy. Some of these studies have also shown a reduction of the needed inhaled corticosteroid dose for some patients when DSCG was added to their treatment regimen (e.g. Petersen et al. Sodium cromoglycate as a replacement for inhaled corticosteroids in mild-to-moderate childhood asthma. Allergy 1996; 51: 870-875). For patients with more severe disease, whose asthma is not optimally controlled despite maximal doses of inhaled corticosteroids, DSCG provides a safe and flexible option for added symptom relief with the promise of lowering the dose of corticosteroids.

Summarised from several studies, it can be stated that the anti-asthmatic effects of DSCG are related to stabilization of the mast cell membrane, suppression of eosinophil activation, suppression of accumulation of T-lymphocytes and eosinophils, suppression of the formation of IL-5 by peripheral mononuclear cells, suppression of excitation of the sensory nerve C-fibre, suppression of the expression of adhesion molecules, and suppression of IgE formation. These findings are based on both in vitro and in vivo evaluations. In the treatment of pulmonary diseases such as asthma and chronic obstructive pulmonary disease (COPD), it is thought to be critical to reduce the inflammatory response in the airways in order to reverse many of the changes seen in these diseases.

Another field where DSCG is often used is the treatment of diseases of the eye. The compound has been shown to have a positive effect when utilized in allergic eye conditions, vernal conjunctivitis, atopic keratoconjunctivitis and giant papillary conjunctivitis. Again, the mechanism of action is based on the stabilization of mast cells.

Furthermore, some antiviral effects are attributed to DSCG. For example, Kazuya et al. (In vitro and in vivo inhibitory effects of disodium cromoglycate on influenza virus infection. Biol Pharm Bull 2004; 27: 825-830) showed in a murine model of respiratory tract infection that DSCG protected mice from death induced by infection with an influenza virus. The effective dose was similar to the dose used in the treatment of asthma. Furthermore, Hashimoto et al. (DSCG reduces RSV-induced illness in RSV infected mice. J Med Virol 2009; 81:354-361) recently showed that mice treated with DSCG are protected against respiratory syncytial virus induced illness and have decreased viral inflammation. However, the mechanism of antiviral action is still being discussed and also the antiviral effect itself remains controversial.

The fact that DSCG is only recommended as an alternative treatment in asthma, is mainly based on the results of two meta-analyses (Tasche at al. Inhaled disodium cromoglycate (DSCG) as maintenance therapy in children with asthma: a systematic review. Thorax 2000; 55:913-920, and van der Wouden at al. Inhaled cromoglycate for asthma in children. The Cochrane Database of Systematic Reviews 2003; 3: CD002173, 1-48). The meta-analyses were performed to overcome the generally small sample size of the available clinical trials with DSCG for the treatment of childhood asthma. Both studies concluded that there is insufficient evidence that DSCG has a beneficial effect as maintenance treatment in children with asthma in comparison with placebo. However, several concerns were raised about the interpretation of the results in these analyses (e.g. Stevens et al. Sodium cromoglicate: an ineffective drug or meta-analysis misused? Pharm Stat. 2007; 6: 123-137). It can be concluded that the clinical efficacy assessment in some of the therapeutic guidelines in childhood asthma is hampered by a major contribution of early clinical trial conduction with limited sample size and suboptimal design, unknown inhaler device performance and discussable conclusions from the two DSCG meta-analyses used as a basis for the guidelines.

Furthermore, the meta-analysis did not consider the possible influence of used delivery systems (metered dose inhalers, dry powder inhalers, and various nebulizer systems). However, it is known that, due to the larger surface area, more severe inflammatory and structural changes occur in the distal lung and lung parenchyma of asthmatic patients (Tulic and Hamid. Contribution of the distal lung to the pathologic and physiologic changes in asthma. Chest 2003; 123: 348S-355S) and that a similar but more severe inflammation process is present in the peripheral airways compared with the central airways in asthma patients (Hamid et al. Inflammation of small airways in asthma. J Allergy Clin Immunol 1998; 101: 386-390). To reach these inflammation sites in the lung, particularly in children, a high percentage of the drug particles should be smaller than 3.3 µm (Keller at al. Using infant deposition models to improve inhaler system design. Proceedings Respiratory Drug Delivery IX, 2004, p. 221-231). The percentage of small particles, and thus the lung deposition, is known to be negatively affected by hygroscopic growth of particles in the humid environment of the respiratory tract (up to 99% relative humidity) (Ferron at al. Estimation of the deposition of aerosolized drugs in the human respiratory tract due to hygroscopic growth. J Aerosol Med 1989; 2: 271-284). DSCG is a very hygroscopic substance and it has been shown in a Next Generation Impactor (NGI), operated at 50 and 95% relative humidity, that the DSCG fine particle fraction declines with increasing humidity and DSCG dose and that this decline is much larger for metered dose inhalers (MDIs) and dry powder inhalers (DPIs) compared to fine mist nebulizers (Keller et al. Importance of the inhaler system and relative humidity on the fine particle dose of disodium cromoglycate. Proceedings Respiratory Drug Delivery Europe 2007, p. 307-310). A solution for this problem is presented in US 2007/0193577, where DSCG is nebulized with high efficiency nebulizers such as vibrating membrane nebulizers (e.g. eFlow nebulizer of PARI Pharma GmbH). The nebulization with such nebulizers results in an unexpectedly high amount of drug deposited in the lungs.

A clinical study (Moeller et al. European Respiratory Society Conference 2008, Poster No. 3958) showed that nebulized DSCG was therapeutically as effective as inhaled steroids. The study lasted for 6 months and compared two children cohorts suffering from atopic allergic asthma. One cohort inhaled 3 times daily IsoCrom (20 mg/2 ml) via a customized small droplet eFlow electronic nebulizer and the other cohort inhaled twice daily steroids via a metered dose inhaler with an AeroChamber. However, nebulization of 3 times 2 ml IsoCrom was rated burdensome, since some children had to inhale 3 times daily up to 10 minutes which compromised drug adherence. Thus, the development of a higher concentrated DSCG solution with the same good tolerability as IsoCrom offering shorter nebulization times and less frequent administration was most desirable.

Currently, DSCG for inhalation often needs to be used four times a day, due to the short half-life of the drug. This multiple dosing generally leads to poor compliance and diminished effectiveness of the treatment. The administered dose of DSCG largely depends on the type of formulation. With MDIs, 2 mg doses have been used, whereas with a DPI or nebulizer, the dose can be increased to 40 mg. It should also be noted that DSCG is rapidly cleared from the lungs, with 75% of the inhaled dose removed after 2 hours and more than 98% within 24 hours (Norris and Holgate, Cromolyn sodium and nedocromil sodium. In: Middleton et al. (eds) Allergy: principle and practice, 1998; St. Louis: Mosby p. 661-667).

In general, it would be an advantage to reduce the number of treatments per day, thereby increasing the compliance and the effectiveness of DSCG. Furthermore, as described above, nebulized DSCG solutions show better results regarding targeting the lower regions of the lungs. Although nebulizers are easier to use for children as MDIs or DPIs, they have the disadvantage of a longer nebulization time. In this respect, it is important for patient compliance that the nebulization time remains as short as possible.

One important issue found for DSCG solutions is the sensitivity to precipitation. EP 0 212 927 describes combined solutions of DSCG and mucolytic agents such as N-acetyl-l-cysteine, where the sensitivity of DSCG to precipitation was related to the relatively high pH (7-9) and the presence of other solutes. Stable solutions were prepared by minimizing the amount of di- and multivalent metal ions and by adding a chelating agent. The latter should ensure that no precipitation of metal salts of the cromoglycate anion occurs. The concentration of the chelating agent depended on the present concentration of metal ions: in case the latter concentration is lower than 0.40 ppm, the chelating agent can be omitted. Even when the chelating agent is incorporated, the concentration of metal ions should be less than 10 ppm. The solution may further contain conventional excipients such as sodium chloride, dextrose or mannitol, and buffers.

EP 0 413 583 describes solutions with from about 0.8 to 5% of cromolyn, where the metal ion concentration can be larger than 20 ppm. Precipitation of cromolyn is in this case prevented on the condition that there is up to about 5% (w/v) of a pharmaceutically acceptable chelating or sequestering agent, preferably sodium citrate dihydrate, added to the solution. The preferred solutions further comprise sodium chloride, potassium chloride, calcium chloride dihydrate, and sodium acetate trihydrate. The salts are used as isotonising agents. Alternatively, the document teaches the use of glycerine, mannitol, or sorbitol as isotonising agents.

EP 0 274 590 mentions that DSCG precipitation in eye drops, caused by metal ions originating from pharmaceutical glass or the rubber or plastic stoppers of vials, or by the presence of preservatives such as benzalkoniumchloride, is generally prevented by the addition of EDTA. However, as allergies to EDTA are often existing, the document presents an alternative solution, being the formulation of DSCG with sorbitol (as isotonising agent) and chlorbutanol (as preservative).

In EP 0 587 264, it is described that DSCG precipitates from highly concentrated solutions (more than 2% DSCG) when sodium chloride is used as isotonising agent. It is suggested to use non-ionic isotonising agents, but the use of usual non-ionic isotonising agents such as sugars and polyols is not preferred as they are considered as growth media for microorganisms. Therefore, the claimed solutions are isotonised with glycerol. The DSCG concentration ranges between 3.5 to 5% (w/v).

In EP 0 933 084, the precipitation of DSCG is related to the presence of benzalkonium chloride and metal ions. The known methods of preventing this are, according to the inventors, the use of chelating agents, sorbitan, castor oil and non-ionic surfactants. The invention described here, is based on the use of 2-amino-ethanol or tocopherol for the prevention of the precipitation. The concentration of the active agent may generally be about 1.5 to 4% by weight. Sodium chloride and glycerine are described as isotonising agents.

US 2007/0193577 describes DSCG solutions for inhalation, including formulations comprising sodium chloride along with relatively small amounts of xylitol or trehalose. The document is silent about the rationale or the effects of such combination of excipients.

In summary, the prior art describing DSCG solutions suggests to avoid precipitation by reducing or avoiding the presence of metal ions, by adding chelating agents, and, when no chelating agents are used, by replacing sodium chloride by non-ionic isotonising agents.

A further important requirement for DSCG solutions for inhalation is that they are well-tolerable and non-irritating in the respiratory tract. Application WO 97/15284 describes that DSCG causes eye irritation, manifested by a strong burning sensation in the eye. This suggests that also irritation on the mucosal surfaces of the respiratory tract might occur. Therefore, attention should be given to possible irritation effects during the development of novel DSCG solutions.

The inventors found that the solutions presented in prior art do not fully solve the problems related to the formulation of highly concentrated DSCG solutions. Firstly, it was found that solutions only containing non-ionic isotonising agents are more irritating in the respiratory tract as solutions where sodium chloride is used. On the other hand, it was found that not only di- and multivalent metal ions seem to have a negative effect in DSCG solutions, but that solutions isotonised with alkali metal salts such as sodium chloride can be difficult to aerosolise. The addition of chelating agents only brings a limited solution to the problem. Therefore, it is an aim of the invention to provide improved DSCG solutions with favourable aerosolisation properties. Further aims will become apparent on the basis of the description and the patent claims.

SUMMARY OF THE INVENTION

The invention relates to formulations for the prevention or treatment of respiratory diseases, in which inflammatory processes are related to the disease or symptoms of the disease. The invention also relates to highly concentrated, stable, well-tolerable and clear liquid aqueous pharmaceutical compositions of a pharmaceutically active agent that can be used to prevent or treat these inflammatory processes.

More specifically, the invention provides sterile liquid aqueous pharmaceutical compositions comprising 2.0 to 10.0% (w/v) of a mast cell stabilizing active agent, preferably disodium cromoglycate (DSCG), and a tonicity-adjusting component, which is a combination of at least one non-ionic tonicity-adjusting excipient and at least one ionic tonicity-adjusting excipient. The molar ratio of the non-ionic tonicity-adjusting excipient to the ionic tonicity-adjusting excipient is at least 1:1. In other words, the molar concentration of the non-ionic tonicity-adjusting excipient is at least as high as the molar concentration of the ionic tonicity-adjusting excipient. The respective molar concentrations are preferably selected to effect a dynamic viscosity of less than about 10 mPa·s.

The solutions can be administered to the upper and lower respiratory tract as an aerosol, where the active agent and the optimised excipient mix are contained in the droplets of the dispersed liquid phase. In another aspect, the solutions can also be used for prevention or treatment of conditions of the eye, ear and skin.

The invention further relates to a method of applying the pharmaceutical composition, said method comprising (a) providing the liquid aqueous pharmaceutical solution as defined above, (b) providing an aerosol generator capable of aerosolizing the solution, and (c) operating said aerosol generator to aerosolize the said solution.

In this embodiment, the invention provides aerosol generators and methods for efficient (i.e. where a large part of the aerosol reaches the target site) and fast nebulization of the formulations. The high concentration and efficient and fast nebulization allow reducing the inhalation times needed to deliver the therapeutic dose to the upper or lower respiratory tract. This is especially advantageous for aerosol delivery of DSCG in children, where it is particularly attractive in view of its excellent safety profile in comparison to corticosteroids.

DETAILED DESCRIPTION OF THE INVENTION

The compositions according to the invention are aqueous solutions well-suited for administration as aerosols.

The term composition refers to a mixture of compounds. Synonyms for composition are formulation and preparation. More specifically, the present compositions are aqueous solutions, referring to liquid single-phase systems wherein the liquid carrier or solvent consists predominantly or completely of water. In specific cases, the liquid carrier can contain small fractions of one or more liquids which are at least partly miscible with water.

The compositions according to the invention are preferably sterile compositions. The term sterility is to be understood in the usual pharmaceutical sense. It is understood as the reduction of the number of germs below a specific concentration, so that, even when they reproduce in the pharmaceutical composition during storage, they cannot cause infection when the composition is applied in an organism. Sterility is to be tested for by suitable tests which are defined in the relevant pharmacopeias.

Several sterilisation methods are available for liquid compositions, such as for example autoclaving and sterile filtration. Sterile filtration is particularly preferred, as this can be implemented in production lines, whereas autoclaving is a batch process. However, not all liquid compositions can be sterile filtered. For example, highly viscous solutions can often not be passed through the narrow pores of a sterilisation filter.

The term active compound refers to a natural, biotechnology-derived or synthetic compound or mixture of compounds useful for the diagnosis, prevention, management, or treatment of a disease, condition, or symptom of an animal, in particular a human. Other terms which may be used as synonyms of active compound include, for example, active ingredient, active agent, active pharmaceutical ingredient, therapeutic compound, drug substance, drug and the like. It should be noted that the term active compound also includes the possible various forms of an active compound, such as salts, solvates, isomers, conjugates, prodrugs or derivatives.

The pharmaceutical solution according to the invention contains disodium cromoglycate (DSCG) as a mast cell stabilizing agent. Commonly used synonyms are sodium cromoglicate and cromolyn sodium. DSCG is an established drug in the treatment of asthma, where it performs its action by inhibiting the inflammatory reactions and cell mediators leading to asthma exacerbations. Other known therapeutically suitable mast cell stabilizing agents are, for example, nedocromil, lodoxamide, and pemirolast.

Furthermore, DSCG showed a positive effect in the treatment of viral infections such as influenza and respiratory syncytial virus induced illness. Due to these anti-inflammatory and anti-infective effects, the formulation according to the invention can also become relevant for the prevention or treatment of other respiratory tract diseases than asthma where inflammatory and/or infectious processes are involved, such as for example chronic obstructive pulmonary disease (COPD).

Further examples of such upper and lower respiratory tract diseases are acute and chronic sinusitis, rhinitis and rhinosinusitis of different causes, allergic rhinitis, nasal polyps, nasal furuncles, epistaxis, nasal and sinonasal conditions related to lower respiratory tract diseases such as nasal and sinonasal conditions related to ear diseases such as inflammations of the ear, allergy, oropharyngeal infections, laryngotracheobronchitis, bronchitis, bronchiolitis, such as diffuse bronchiolitis and bronchiolitis obliterans, bronchiectasis, alveolitis, pneumonia such as community acquired pneumonia, hospital acquired pneumonia, ventilator associated pneumonia, healthcare associated pneumonia, aspiration pneumonia, lipid pneumonia, eosinophilic pneumonia, chemical pneumonia, atypic pneumonia and severe acute respiratory system disease, pulmonary infections with or without acute exacerbations, such as bacterial, viral, fungal, and protozoal infections of the respiratory tract, emphysema, sarcoidosis, tuberculosis, nontuberculous mycobacterial pulmonary diseases, parenchymatic and/or fibrotic diseases or disorders including cystic fibrosis and idiopathic pulmonary fibrosis, pulmonary arterial hypertension, interstitial lung diseases, pertussis, and graft rejection after lung, stem cell, or bone marrow transplantation.

Furthermore, the DSCG compositions can also be used for treatment of eye, ear or skin conditions where inflammatory and/or infectious processes are involved, such as for example allergic eye conditions, vernal conjunctivitis, atopic keratoconjunctivitis and giant papillary conjunctivitis. In such an embodiment, the solution may be applied as an aerosol or may be filled into a glass or plastic bottle fitted with a dropper or spray pump for administration into the eye, nose or ear or onto the skin.

Additionally, the claimed formulations might be useful for an inhaled (supportive) treatment of lung tumors and metastases, based on their mast cell stabilizing effect. Several authors suggested that mast cells play an important role in angiogenesis within developing tumors and in tumor spread and metastasis. This was related to mediators released by mast cells that accumulate at the boundary between healthy tissues and malignancies. Therefore, the prevention of the release of these mediators by mast cell stabilizers may lead to tumor regression.

The concentration of DSCG in the liquid composition of the invention and in the dispersed phase of the aerosol prepared therefrom is preferably high. A high concentration has several advantages in formulations for inhalation, such as easier reaching of the therapeutic concentration at the target site, reduction of the volume needed to be inhaled to reach the therapeutic concentration at the target site and therefore reduction of the nebulization time, longer period of action and therefore reduction of the frequency of application. The latter is also a major reason for using highly concentrated formulations when applying the formulations to the eye.

Preferably, the concentration of the active compound, i.e. the DSCG, is in the range from about 2 to about 10% (w/v), preferably in the range from 4.0 to 8.0% (w/v) or in the range from 4.0 to 6.5% (w/v), such as about 4.0, 4.5, 5.0, 5.5, 6.0, 6.5, 7.0, 7.5, 8.0, 8.5, 9.0, 9.5, or 10.0% (w/v). A particularly preferred concentration is about 6.0% (w/v).

In order to be well-tolerated, a pharmaceutical composition for application to the respiratory tract or the eye should, as far as possible, have a physiologic tonicity or osmolality. For achieving an acceptable osmolality, a tonicity-adjusting component is incorporated in the compositions of the invention. As used herein, a tonicity-adjusting component is understood as one or more pharmaceutical excipients which are osmotically active and which are used in common practice for the purpose of adjusting the osmolality or tonicity of liquid pharmaceutical formulations. In contrast, the term is not understood as including those excipients which, even though they are osmotically active, are primarily used for different purposes. For example, citric acid would contribute to the osmolality of a pharmaceutical solution, but it would not normally be incorporated for the purpose of producing this effect, but rather as a pH-modifier.

The amount of the tonicity-adjusting component in the compositions should be selected to yield an osmolality close to about 290 mOsm/kg, i.e. the osmolality of physiological fluids. Optionally, the osmolality might be higher than 290 mOsm/kg, as it has been found that hypertonic or hyperosmotic solutions might have additional advantages in certain respiratory conditions. The main advantage of hypertonic solutions is related to an increased mucus clearance in diseases accompanied with an undesired mucus production. Therefore, the osmolality of the liquid composition of the invention is therefore preferably in the range of 200 mOsm/kg to 1500 mOsm/kg. More preferred is an osmolality ranging between 200 mOsm/kg and 1200 mOsm/kg, and even more preferred is an osmolality ranging between 250 mOsm/kg and 350 mOsm/kg.

According to the invention, the appropriate osmolality is achieved by incorporating a tonicity-adjusting component which comprises at least one non-ionic tonicity-adjusting excipient and at least one ionic tonicity-adjusting excipient. Moreover, the molar ratio of the non-ionic tonicity-adjusting excipient(s) to the ionic tonicity-adjusting excipient(s) is at least 1:1. The molar ratio is defined in terms of the molar amounts (i.e. number of moles) or molar concentrations and is not to be confused with the mass ratio. While the mass ratio of the non-ionic tonicity-adjusting excipient(s) to the ionic tonicity-adjusting excipient(s) may be less than 1:1, the molar ratio must be at least 1:1.

The inventors found that the use of the most commonly used tonicity-adjusting excipient, sodium chloride, is problematic in combination with DSCG. In particular when high DSCG concentrations are desired, sodium chloride leads to a strong increase of viscosity. This viscosity increase might cause problems during sterile filtration and during nebulization of the formulations. Furthermore, the inventors believe that the high viscosity is a factor that is possibly related to an increased risk of precipitation of DSCG from the highly concentrated solutions.

However, when using an alternative tonicity-adjusting excipient such as a sugar alcohol instead of sodium chloride, the inventors found that the resulting solutions produced more irritation of the mucosal surfaces and cough induction when administered in aerosolised form.

Surprisingly, the inventors have now found that these irritations can be avoided by formulating the DSCG solution with a combination of at least one ionic tonicity-adjusting excipient such as sodium chloride and at least one non-ionic tonicity-adjusting excipient such as mannitol. Just as surprising is that the viscosity increase at certain DSCG concentrations is much less for the latter combination of excipients as expected from interpolating between the viscosities of concentrated DSCG solutions isotonised either with sodium chloride or with a non-ionic tonicity-adjusting excipient, respectively.

The unexpected beneficial properties appear to be present only when the molar concentration of the non-ionic tonicity-adjusting excipient is relatively high compared to that of the ionic tonicity-adjusting excipient. More specifically, the molar ratio of the non-ionic tonicity-adjusting excipient to the ionic tonicity-adjusting excipient (hereinafter also abbreviated as "ratio") is at least about 1:1. In further embodiments, this ratio is at least about 2:1, such as about 3:1. In the case that more than one non-ionic tonicity-adjusting excipient and/or more than one ionic tonicity-adjusting excipient is used, the ratio expresses the sum of the molar concentrations of the non-ionic tonicity-adjusting excipients to the sum of the molar concentrations of the ionic tonicity-adjusting excipients.

The non-ionic tonicity-adjusting excipient can be selected from, for example, the group of carbohydrates. Examples of carbohydrates that can be used for isotonisation are sugars such as glucose, lactose, sucrose and trehalose, and sugar alcohols such as mannitol, xylitol, sorbitol, and isomaltol. Particularly preferred tonicity-adjusting agents are sugar alcohols, and more specifically mannitol and xylitol. In a particular embodiment of the invention, however, the non-ionic tonicity-adjusting excipient is not a cyclodextrin.

The ionic tonicity-adjusting excipient can be selected from, for example, alkali metal salts, such as sodium and potassium salts. Examples of such salts are sodium chloride, sodium gluconate, sodium pyruvate, and potassium chloride. It is possible to use one single ionic tonicity-adjusting agent or a mixture of such agents. The salts may be either added or formed in situ due to a salt formation process.

In one of the preferred embodiments, the concentration of the ionic tonicity-adjusting excipient or excipients, in particular if sodium chloride is used, is kept below approximately 0.1 mol/l, or even below about 0.09 mol/l, such as in the range from about 0.01 to about 0.085 mol/l or in the range of about 0.03 to about 0.05 mol/l. In the preferred embodiments, the non-ionic tonicity-adjusting excipient or excipients are incorporated at a concentration of at least about 0.03 mol/l, more preferably at least about 0.04 mol/l, at least about 0.05 mol/l, at least about 0.07 mol/l or at least about 0.1 mol/l, in particular in the range from about 0.03 to about 0.1 or 0.2 mol/l. Depending on the actually selected excipient(s) and the concentration of DSCG in the solution, other concentrations may however be feasible as well.

As described above, the dynamic viscosity of the liquid compositions for inhalation is important, as a too high viscosity can cause problems during sterile filtration and during nebulization of the formulations. Regarding sterile filtration, a high viscosity might make it difficult to pass the liquid through the pores of the filter. Regarding nebulization, it was found that viscosity has a clear influence on the particle size distribution of the aerosol and on the efficiency of nebulization. Furthermore, a high viscosity might be related to an increased risk of DSCG precipitation from highly concentrated solutions. Therefore, the viscosity should preferably be below about 10 mPa·s. Preferably, the viscosity should be adjusted to not more than about 8 mPa·s. According to a further embodiment, the viscosity is selected in the range from about 2 to about 6 mPa·s. The dynamic viscosity is to be understood as measured at room temperature.

By means of the present invention, such viscosities can be achieved even at relatively high DSCG concentrations, such as 4 to 10% (w/v), even in the presence of sodium chloride. Depending on the selected DSCG concentration, the exact molar ratio of the non-ionic tonicity-adjusting excipient to the ionic tonicity-adjusting excipient may be selected such that the viscosity is in the desired range, i.e. below about 10 mPa·s, or not more than 8 mPa·s, or from about 2 to about 6 mPa·s, respectively. On the other hand, the total amount or concentration of tonicity-adjusting excipients is selected to achieve the desired osmolality of the solution, as described above.

The high viscosity might also have a negative impact in formulations for application to the eye. Also these formulations need to be sterile, which is most economically obtained by sterile filtration. Furthermore, the presumed increased risk of precipitation of DSCG when the viscosity is higher also applies for formulations for application to the eye. As DSCG is often applied in inflammatory conditions of the eye, where a high concentration is preferred due to the general short residence time in the eye, the formulations according to the invention are also relevant for treatment or prevention of conditions of the eye, even though they are not aerosolized but rather dropped in the eye.

Next to tonicity-adjusting excipients, the pharmaceutical composition can contain further excipients such as antioxidants, surfactants, excipients for sustained release or prolonged local retention, excipients for adjusting or buffering the pH, taste-masking agents, sweeteners, and flavours. These excipients are used to obtain an optimal pH, viscosity, surface tension and taste, which support the formulation stability, the aerosolization, and/or the tolerability of the formulation upon inhalation.

Antioxidants are natural or synthetic substances which prevent or interrupt the oxidation of active agents and/or oxidative injury in stressed tissues and cells. These are primarily adjuvants which are oxidisable themselves (i.e. primary antioxidants) or act as reducing agents (i.e. reducing antioxidants), such as, for example, tocopherol acetate, lycopene, reduced glutathione, catalase, and peroxide dismutase. Other adjuvants used to prevent oxidative reactions are synergistic antioxidants, which do not directly act in oxidation processes, but indirectly via the complexation of metal ions that are known to catalyse oxidation reactions. Frequently used synergistic antioxidants are ethylenediamine tetraacetic acid (EDTA) and its derivatives. Further useful antioxidants (primary, reducing and/or synergistic antioxidising working mechanism) are ascorbic acid and its salts, esters of ascorbic acid, fumaric acid and its salts, malic acid and its salts, citric acid and its salts, butyl hydroxy anisole, butyl hydroxy toluene, propyl gallate, sulphites such as sodium metabisulfite, and maltol.

The sodium salts of specific acids, such as sodium gluconate and sodium pyruvate are interesting agents as they can be used both as ionic tonicity-adjusting agent and anti-oxidising agent. It was previously described that the magnesium salt of gluconic acid, amongst other magnesium salts, has an anti-oxidising effect on stressed tissues and cells. The magnitude of the latter effect seems to depend on the type of anion, where the gluconate salt of magnesium was found to be more potent than for example magnesium sulphate or magnesium chloride. It can therefore be presumed that also the sodium gluconate salt will have a certain anti-oxidising effect on stressed tissues and cells, which can be particularly advantageous in the treatment of inflammations. Similarly, sodium pyruvate has been described to have in vivo anti-oxidising effects.

Preferably, the pH value of the formulation lies in the slightly acidic to neutral region, i.e. the solution preferably has a pH value ranging between about 4 to about 7. A pH in the range of about 5 to about 7 is particularly preferred.

The composition can comprise one or more excipients to adjust and/or buffer the pH value of the solution. For adjusting and, optionally, buffering pH value, physiologically acceptable acids, bases, salts, and combinations thereof may be used. Excipients often used for lowering the pH value or for application as acidic component in a buffer system are strong mineral acids, in particular sulphuric acid and hydrochloric acid. However, more preferably, inorganic and organic acids of medium strength as well as acidic salts may be used, such as, for example, phosphoric acid, citric acid, tartaric acid, succinic acid, fumaric acid, methionine, acidic hydrogen phosphates with sodium or potassium, lactic acid, and glucuronic acid. Excipients suitable for raising the pH or as basic component in a buffer system are, in particular, mineral bases such as sodium hydroxide or other alkali and alkaline earth hydroxides and oxides such as, for example, magnesium hydroxide and calcium hydroxide, ammonium hydroxide and basic ammonium salts such as ammonium acetate, as well as basic amino acids such as lysine, carbonates such as sodium or magnesium carbonate, sodium hydrogen carbonate, and citrates such as sodium citrate.

The composition can also comprise a buffer system consisting of two components. One of the most preferred buffer systems contains citric acid and sodium citrate. Nevertheless, other buffering systems may also be used.

Furthermore, the surface tension of a liquid composition is important for an optimal nebulization of the claimed solutions. The surface tension should range between about 25 and 80 mN/m, and more preferably between 30 to 75 mN/m. Formulations with a surface tension in the lower part of this range are expected to show a good spreadability of the preparation on the mucous membranes of the respiratory tract, but these lower surface tensions generally lead to reduced quality of the aerosol and a reduced efficiency of the nebulization. Furthermore, the surface tension might need to be adjusted to allow a good emptying of the formulation from its primary package.

Surfactants can be included to adjust the surface tension for the above described reasons, and further for stabilization, taste-masking and/or sustained release. In this context, surfactants are defined as surface-active materials, having at least one relatively hydrophilic and at least one relatively lipophilic molecular region. Surfactants can also be referred to as detergents, tensides, emulsifiers or wetting agents. These materials accumulate at hydrophilic-lipophilic phase interfaces and reduce the surface tension. The surface-active materials can be ionic or non-ionic. Preferably, non-ionic surfactants are used which are surfactants that have no real ionic charge in aqueous media at substantially neutral pH (for example at a pH between 4 and 7), but, at most, partial charges. Particularly preferred non-ionic surfactants are those that have a good physiological compatibility and that are considered safe for oral or nasal inhalation. Preferred non-ionic surfactants are, for example, tyloxapol, polysorbates, such as polysorbate 80, vitamin E TPGS, and macrogol hydroxystearates, such as macrogol-15-hydroxystearate. The non-ionic surfactant component might also comprise a mixture of two or more surfactants, such as polysorbate 80 in combination with vitamin E TPGS.

The total content of the surfactant component in solutions for oral or nasal inhalation should be limited to a maximum of about 5% (w/v) in order to avoid mucosal irritation. Particularly preferred concentrations are between about 0.01 to about 2.0% (w/v), and between about 0.02 to about 1% (w/v).

Further excipients useful in formulations for inhalation are taste-masking agents. A bad taste of formulations for inhalation is extremely unpleasant and irritating. The bad taste sensation results from direct deposition of aerosol droplets in the oral and pharyngeal region upon oral inhalation, from transport of drug from the nose to the mouth upon nasal inhalation, and from transport of the drug from the respiratory tract to the mouth related to the mucociliary clearance in the respiratory system. As used herein, a taste-masking agent is any pharmaceutically acceptable compound or mixture of compounds capable of improving the taste of an aqueous system, regardless of the mechanism by which the improvement is brought about. For example, the taste-masking agent may cover the poor taste, i.e. reduce the intensity by which it is perceived, or it may correct the taste by adding another, typically more pleasant, flavour to the composition, thereby improving the total organoleptic impression. Other taste-masking mechanisms are complexation, encapsulation, embedding or any other interaction between drug and other compounds of the composition.

The taste-masking agent can be selected from the group of pharmaceutically acceptable sweeteners, such as, for example, saccharin, aspartame, cyclamate, sucralose, acesulfame, neotame, thaumatin, and neohesperidine, including salts and solvates thereof, such as, for example, the sodium salt of saccharin and the potassium salt of acesulfame. Furthermore, sugars such as sucrose, trehalose, fructose, and lactose, or sugar alcohols, such as xylitol, mannitol, and isomalt can be used. Further useful taste-masking agents include pharmaceutically acceptable surfactants, alkali or alkaline earth metal salts, organic acids, such as citric acid and lactic acid, and amino acids, such as arginine. Also aromatic flavours, such as the ingredients of essential oils (such as menthol, thymol and cineol) may be used to improve the taste and tolerability of the claimed formulations.

The preferred concentration of sweeteners such as saccharin sodium or aspartame, ranges from about 0.01 to about 3% (w/v), in particular from about 0.025 to about 1% (w/v), whereby the concentration of ionic sweeteners will depend on the concentration of other ionic substances included in the formulation. In this respect, it has been found by the inventors that the molar concentration of ionic substances in highly concentrated solutions should remain below the molar concentration of non-ionic tonicity adjusting agents, in order not to increase the viscosity of the formulation too much. The preferred concentration of other taste-masking agents will depend on their taste-masking intensity and on their contribution to the osmolality of the formulation, as described above.

It is noted that when the tonicity-adjusting component is a combination of a salt such as sodium chloride and a sugar or sugar alcohol, a neutral and well-acceptable taste is achieved, providing a further advantage of this particular embodiment of the invention. In this case, the incorporation of further taste-masking or taste-improving excipients appears unnecessary.

According to a further aspect of the invention, the pharmaceutical solutions described herein are used as medicaments. Their particular usefulness is based, inter alia, on the fact that, due to the high concentration of the active compound, they enable the convenient administration of relatively large doses. For example, when administered in nebulised aerosol form, a high concentration allows for a short nebulisation time.

In particular, the compositions of the invention are useful as medicaments for the treatment of asthma and other respiratory diseases involving inflammation and/or infection, such as asthma and chronic obstructive pulmonary disease (COPD). Due to the high concentration of the active ingredient, the compositions are also useful for reducing the dosing interval, such as in aerosol therapy using DSCG as active compound. In this case, the dosing interval may be reduced to a once- or twice daily administration regimen.

As mentioned, the compositions provided by the present invention are, according to a preferred embodiment, administered as aerosols. An aerosol is defined herein as a system comprising a continuous gas phase and, dispersed therein, a discontinuous or dispersed phase of liquid and/or solid particles. Aerosols comprising a dispersed liquid phase and a continuous gas phase are sometimes referred to as "liquid aerosols" or, probably more appropriately, "aerosolized liquids".

In the current invention, the dispersed phase essentially consists of liquid droplets preferably having a mass median aerodynamic diameter from about 1.5 to about 6 μm. The droplets of the dispersed phase comprise the mast cell stabilizing active agent in a liquid environment. The liquid environment is mainly an aqueous phase, with or without further excipients as described above. Preferably, the liquid phase is a solution. It will be understood by the person skilled in the art, that the features and preferences with respect to the liquid composition, as disclosed herein-above, may also be applied to the dispersed phase of the aerosol generated therefrom and vice versa.

The continuous gas phase of the aerosol may be selected from any gas or mixture of gases which is pharmaceutically acceptable. For example, the gas may simply be air or compressed air, which is most common in inhalation therapy using nebulizers as aerosol generators. Alternatively, other gases and gas mixtures, such as air enriched with oxygen, carbon dioxide, or mixtures of nitrogen and oxygen may be used. Most preferred for the current invention is the use of air as continuous gas phase.

The dispersed phase of the aerosol prepared from the compositions of the invention exhibits a mass median aerodynamic diameter (MMAD) preferably from about 1 to about 6 μm and more preferably from about 2 to about 4.5 μm or from about 1.5 to about 4 μm. The MMAD is measured using cascade impaction methods for liquid aerosols and describes the diameter below which 50% of the aerosolized drug mass is contained, in other words, 50% of the drug mass is contained in droplets having a diameter smaller than the MMAD.

Another parameter describing the dispersed phase of the aerosol is the particle size distribution of the aerosolized liquid particles or droplets. The geometric standard deviation (GSD) is an often used measure for the broadness of the particle or droplet size distribution of generated aerosol particles or droplets.

The selection of the precise MMAD within the above described range should take the target region or tissue for deposition of the aerosol into account. For example, the optimal droplet diameter will differ depending on whether oral or nasal inhalation is intended, and whether oropharyngeal, bronchial, pulmonary, nasal, and/or paranasal sinus delivery is focussed upon. Additionally, the age of the patients and their breathing pattern belong to the important factors determining the optimal particle size for drug delivery to the lungs.

If the aerosol is intended for prevention or treatment of a disease or condition of the oropharynx or the nasal cavity via, for instance, a spray pump, the MMAD should be larger than about 9 μm. For the treatment of the upper airways, in particular the sinonasal mucosa, osteomeatal complex, and paranasal cavities, an MMAD in the range from 2 to 4 μm is particularly suitable. However, the volume and geometry of the nose and sinuses and the diameter of the ostia through which the aerosol reaches the sinuses are known to differ substantially between individuals. Therefore, if the individual sinonasal anatomy or a physiological parameter derived from the sinonasal anatomy of a person to be treated with an aerosol is at least partially known, it may be possible to select a particular MMAD for optimised sinonasal or sinus delivery. In some embodiments, the aerosol prepared according to the invention may have an MMAD of about 2.5 to about 4.5 μm, in others from about 3 to about 4 μm, or from about 2.0 to about 3.5 μm. In further embodiments, the MMAD is approximately 2.0 μm, 2.5 μm, 3.0 μm, 3.2 μm, 3.4 μm, 3.6 μm, 3.8 μm, or 4.0 μm.

On the other hand, if the aerosol is intended for pulmonary delivery, it preferably has an MMAD below 5.0 μm. Preferably, the MMAD is in the range from about 2.0 to about 4.5 μm and a GSD in the range from about 1.2 to about 2.2, preferably from about 1.2 to about 1.8, or more preferably, from about 1.4 to about 1.6. Such particle size and particle size distribution parameters are particularly useful to achieve a high local drug concentration in the lungs, including the bronchi and bronchioli, relative to the amount of drug which is aerosolized. In this context it must be considered that deep lung deposition requires smaller MMADs than deposition in the central airways and that for babies and younger children smaller droplet sizes in the range from about 1.5 to about 3 μm are more preferred.

Due to the different dimensions of the respiratory tract in adults and children, the invention provides for aerosols with a high fraction of droplets smaller than 5 μm and smaller than 3.3 μm, respectively. The need for smaller droplets in children is supported by the fact that lung deposition from currently available nebulizers and pMDI/spacers ranges from about 8% to about 45% of the nominal dose in adults, whereas the lung deposition of aerosols generated by the same nebulizers in young children was shown to range between about 0.67 and about 5.4% of the nominal dose. Hence, administration of smaller droplets in a size range characterized by MMADs from about 1.5 to about 3 μm are more preferable for children younger than 3 years, since a higher lung deposition can be obtained which would require on the other hand lower nominal doses for administration.

The excellent safety profile of DSCG makes it very interesting as an asthma controlling medication in children, as an alternative to the inhaled corticosteroids, which generally have side effects, such as growth retardation. However, the use of DSCG in childhood asthma is in steep decline, probably related to the inability of current nebulizers to reach the target region, namely the narrow lower airways of the children. A first problem for reaching the lower airways in children can be a too large droplet size of the aerosol. Secondly, young children often need to be treated with a face mask. As young children mainly breathe through the nose, and as the nose is a good droplet/particle filter, the lung deposition is significantly lower as when the aerosol is applied via oral inhalation. Furthermore, the respiratory breathing pattern of infants differs from that of adults with respect to the tidal volume and the respiratory rate. This may be too low to keep up with the driving flow of many commercial nebulizer compressor configurations, resulting in large aerosol losses. These factors all lead to the reduction of the dose of active substance reaching the site of action and therefore to a reduced pharmacological effect of the active compound. However, optimizing the aerosol particle size parameters and delivery parameters might improve the delivered dose and the effect of the drug, thereby increasing the efficiency of the drug. Preferably, the aerosol contains at least about 30% of the nominal dose in droplets smaller than 3.3 μm when applied to children.

The aerosol can be generated with any conventional aerosol generator. As used herein, an aerosol generator is a device or a combination of devices capable of generating and emitting an aerosol. According to the present invention, the device is capable of aerosolizing a liquid material into a dispersed liquid phase. Typically, such device is referred to as a nebulizer. Depending on the type and model of the device, the aerosol generator of the invention may require or include a compressor. In other words, the term aerosol generator is used for the complete apparatus or assembly required to produce and emit an aerosol and to administer the aerosol to an animal or to a human patient. Preferably, the nebulizer is selected from jet, ultrasonic, piezoelectric, jet collision, electrohydrodynamic, capillary force, perforated membrane, or perforated vibrating membrane nebulizers. In children, the nebulisers are often used with a face mask. The tidal volume for toddlers and babies requires that the dead volume of a face mask is as small as possible to avoid an oxygen deficit during inhalation. Hence, drug delivery to children younger than 3 years should be optimized by a number of means, such as soft, non-irritating face masks with a low dead volume securing sufficient oxygen supply, small droplets and noiseless drug administration of non-irritating drug formulations.

A preferred aerosol generator for application of an aerosol in the upper respiratory tract is a nebulizer generating the aerosol via a perforated vibrating membrane principle as known for eFlow, but which is also capable of emitting a pulsating aerosol. This type of nebulizer has a nose piece for directing the aerosol flow into the nose. For smaller concentrations of DSCG, also the combination of the PARI SINUS™ compressor and a jet nebuliser can be used. Aerosols generated by such modified electronic or jet nebulizers can reach sinonasal or paranasal cavities much better than when the aerosol is generated in a continuous mode. The pulsating pressure waves achieve a more intensive ventilation of the sinuses so that a concomitantly applied aerosol is better distributed in these cavities. Examples for such electronic nebulization devices are disclosed in WO 2009/027095.

If the intended use is the delivery of the active agent to an affected (or potentially affected) site of the lower airways such as the bronchi or the deep lungs, it is particularly preferred that a piezoelectric, electro-hydrodynamic, or perforated membrane-type nebulizer is selected for generating the aerosol. Examples of suitable nebulizers include the Mystic™, I-Neb™, MicroAir™, Multisonic™, Respimate™, eFlow™, AeroNeb™, AeroNeb PrO™, and AeroDose™ device families. A particularly preferred nebulizer for targeting the drug to the lower respiratory tact is the eFlow electronic vibrating membrane nebulizer.

Another particularly preferred nebulizer concept is the investigational eFlow Closed System as described in DE 10 2005 038 619. This system is an adapted vibrating membrane nebulizer wherein an ampoule containing a drug solution can be inserted in the closing cap of the nebulizer reservoir. The ampoule, as described in DE 10 2007 056 462.9, is only opened when the nebulizer cap is closed by an opening system incorporated in the nebulizer. This allows the drug solution to immediately flow in the nebulizer reservoir, thereby leading to a more reproducible and accurate dosing associated with reduced aerosol losses.

The inventors found that the novel DSCG formulations can reproducibly be nebulized via vibrating membrane type nebulizers, such as eFlow and the investigational eFlow Closed System, whereas this was not possible with a jet nebulizer at relative humidities of about 50% and a constant flow at 15 l/min. This effect was most likely related to the evaporation of water from the nebulizer reservoir, leading to an increasing concentration of DSCG in the liquid, eventually leading to a higher viscosity of the solution. Such effects could not be observed when using eFlow type nebulizers protecting the inventive formulations from evaporation. According to a further preference, the nebulizer is designed so that at least 40% of the loaded formulation and corresponding dose is delivered ex mouthpiece or via a face mask as an aerosol. More preferably, at least 50% of the dose in the liquid composition filled into the nebulizer is actually emitted from the device as an aerosol, which is best achieved by an electronic vibrating perforated membrane nebulizer. According to another embodiment, at least about 50% of the emitted aerosol contains droplets with a diameter of less than 5 μm.

Whether adapted for pulmonary or sinonasal delivery, the nebulizer should preferably be selected or adapted to be capable of aerosolizing a unit dose at a preferred output rate. A unit dose is here defined as a volume of the liquid composition comprising the effective amount of active compound designated to be administered during a single administration. Preferably, the nebulizer can deliver such a unit dose at a rate of at least about 0.1 ml/min or, assuming that the relative density of the composition will normally be around 1, at a rate of at least about 100 mg/min. More preferably, the nebulizer is capable of generating an output rate of at least about 0.15 ml/min or 150 mg/min, respectively. In further embodiments, the output rates of the nebulizer are at least about 0.2, 0.3, 0.4, 0.5, 0.6, 0.7, 0.8, 0.9 or 1 ml/min delivering an aerosol with an MMAD in the range from about 2 to about 4 μm.

Furthermore, the output rate of the nebulizer should be selected to achieve a short nebulization time of the liquid composition. Obviously, the nebulization time will depend on the volume of the composition which is to be aerosolized and on the output rate. Preferably, the nebulizer should be selected or adapted to be capable of aerosolizing a volume of the liquid composition comprising an effective dose of the active compound within not more than about 20 minutes. More preferably, the nebulization time for a unit dose is not more than about 10 minutes. In a further embodiment, the nebulizer is selected or adapted to enable a nebulization time per unit dose of not more than about 6 minutes, and more preferably not more than about 3 minutes. Presently most preferred is a nebulization time in the range from about 0.5 to about 3 minutes.

The volume of the formulations is preferably low in order to allow short nebulization times. The volume, also referred to as the volume of a dose, or a dose unit volume, or a unit dose volume, should be understood as the volume which is intended for being used for one single administration. Specifically, the volume may be in the range from about 0.3 to about 3.5 ml, preferably about 0.4 to about 3.5 ml. In case a residual volume is desired or helpful, this residual volume should be less than 1 ml, more preferably less than 0.5 ml, and most preferably less than 0.2 ml. The effectively nebulized volume is then preferably in the range from about 0.1 to about 2.5 ml or about 0.25 to about 2.5 ml, or more preferably in a range from about 0.2 to about 1.5 ml or about 0.5 to about 1.5 ml.

In a particular embodiment, the solution provided by the invention is administered by means of a perforated membrane type nebulizer for the generation of an aerosol from an aqueous pharmaceutical solution comprising disodium cromoglycate, wherein the following features are also present:

(a) a nominal dose of at least 40 mg of disodium cromoglycate is aerosolised within less than 3 minutes;

(b) the actually delivered dose via the mouthpiece of the nebuliser is more than 50% of the nominal dose of disodium cromoglycate;

(c) the fraction of the dose of disodium cromoglycate which is delivered as fine particles having a diameter below 3.3 μm is more than 30% of the nominal dose; and (d) the volume of the solution comprising a single unit dose is not more than 1.5 ml.

In one embodiment, the following feature is also present:

(e) the aerodynamic droplet size distribution pattern as measured in a Next Generation Impactor operated at 15 l/min and a temperature of 23° C.±5° C. and relative humidities between 30% and 99% does not deviate by more than 20%.

In a further aspect, the invention provides a method for preparing the aqueous liquid composition defined hereinabove. The method comprises the steps of (a) providing the ingredients of the composition; (b) combining the ingredients provided in step (a) to form an aqueous liquid composition; (c) sterile filtration of the composition obtained in step (b); and (d) filling the sterile filtered composition obtained in step (c) into sterile containers under aseptic conditions. The steps (a) to (d) are conducted in this sequence.

Optionally, the method may include further steps, and each of the steps (a) to (d) may comprise a number of substeps. For example, it may be useful to first sterilise one or more ingredients in order to provide them in sterile form. In this way, the bioburden is kept relatively low with the effect that the sterile filtration step (c) will be less problematic to design.

Subsequently, sterile filtration of the resulting aqueous solution is conducted. How to select an appropriate filter and conduct the sterile filtration process is per se known to a person trained in the field. Typically, one or two filtrations through filters having a pore size of 0.22 μm, optionally with a pre-filter with a pore size of 0.45 μm, are recommended.

The subsequent filling of the sterile solution into the final containers is performed under aseptic conditions. Pre-sterilised glass vials may be selected as containers. More preferably, sterile plastic vials which are manufactured in-line using a blow-fill-seal process design are used, in particular if the product is packaged as single dose units with a dose volume in the range from about 0.2 to about 5 ml.

The primary packaging means can be glass containers (for example, vials) or plastic vials. However, the inventors found that care should be taken not to use rubber closure devices, as contact of the claimed formulation with this closure device material can lead to precipitation of DSCG. Therefore, the closure devices are preferably coated with an inert material, such as for example Teflon. On the other hand, the solutions can also be filled in sealed plastic containers such as polypropylene (PP) or polyethylene (PE) vials which may advantageously be formed, filled and sealed by the blow-fill-seal method, which is well known to the technically qualified person in the field. The thus produced containers are suitable, in particular, for liquid goods with a volume starting from about 0.2 ml. Alternatively, blisters made of aluminium or aluminium coated polymers or other suitable polymeric material mixtures may be used as packaging material for a unit dose application allowing an aseptic filling of the liquid drug formulation.

Blow-fill-seal vials may be formed in a bottle shaped design with a closure which can be removed by twisting or bending. The thus formed opening allows a dropwise dosing and entire emptying, meeting a dispensing uniformity as claimed by Pharmacopoeias. The opening may further be designed such that it fits onto a luer connection or luer lock connection. Thus, the opening may have a round shape and a diameter which largely corresponds to the outer diameter of a male luer connection. In this way, a common syringe with luer connection could be connected tightly to the container, for example, in order to take up the contents of the container and transfer it to a nebulizer. Alternatively, the opening may have a smaller diameter, such as the inner diameter of a male luer connective piece, if the opening is within a protrusion which is connectable with a female luer piece.

Even more preferred, the blow-fill-seal vial may be designed so that it may be connected essentially tightly with a connection piece of a correspondingly adapted nebulizer, whereby it is possible to fill the preparation directly into the reservoir of the inhaler as described in DE 10 2005 038 619. An example for such an adapted nebulizer is the eFlow Closed System vibrating membrane nebulizer. The vial is placed in the cover lid of the nebulizer reservoir and pierced by fitting the cover lid on the nebulizer. This system ensures that no drug will be spilled when filled into the medication cup of a nebulizer and the recommended dose will be dispensed as claimed in the medication label.

Plastic containers of the above-mentioned kind are advantageous because they can easily be provided with imprints. Thereby, one can firstly do away with paper labels, which is desirable in order to avoid the migration of components of the adhesive, the paper or the printing ink through the container wall into the preparation. Furthermore, important information may be made available to visually impaired patients by such an imprint. The imprint can contain various information, such as lot number, expiry date, product designation, instructions for use, or one or more volume or dose markings. Especially for paediatric or elderly patients, where a flexible dosing depending on the age and body size is desirable, a pluralityy of volume markings can serve to facilitate the removal of the desired dose without further implements, thereby reducing the risk of dosing errors.

One or more primary packaging means may be packaged in one secondary packaging means, such as a cardboard box.

The following examples serve to illustrate the invention; however, these are not to be understood as restricting the scope of the invention.

EXAMPLES

Example 1

The following example shows the influence of the presence of ions (in the form of sodium chloride) on the viscosity of DSCG solutions. The example is for comparison.

4% DSCG solutions containing increasing concentrations NaCl were prepared. The concentrations are shown in Table 1. In all cases, DSCG was weighed together with sodium chloride and dissolved in water for injection. The dynamic viscosity of the samples was measured at room temperature immediately after preparing the samples with a rotational viscometer. As shown in Table 1, the dynamic viscosity increased strongly for increasing NaCl concentrations.

TABLE 1

Dynamic viscosity of DSCG solutions containing increasing concentrations of sodium chloride

| Formulation | DSCG concentration (% w/v) | NaCl concentration (% w/v) | NaCl concentration (mol/l) | Dynamic viscosity (mPa · s) |
|---|---|---|---|---|
| 1 | 4.0 | 0.0 | 0.000 | 1.12 |
| 2 | 4.0 | 0.5 | 0.086 | 1.40 |
| 3 | 4.0 | 0.9 | 0.154 | 3.49 |
| 4 | 4.0 | 1.5 | 0.257 | 27.06 |
| 5 | 4.0 | 2.0 | 0.342 | 60.96 |
| 6 | 4.0 | 3.0 | 0.513 | 143.39 |

Example 2

In this example, the influence of an increasing DSCG concentration and the type of tonicity-adjusting excipient on the dynamic viscosity of the resulting solution is shown. Table 2 displays the composition of the formulations containing various concentrations of DSCG and various excipients, together with their dynamic viscosity. All solutions were prepared by weighing the active agents and excipients and dissolving these compounds in water for injection. The solutions were sterile filtered and filled in glass vials closed with Teflon-coated stoppers. It is apparent that the increased dynamic viscosity is linked with increasing drug concentrations and increasing ionic excipient concentrations.

Figure 1:
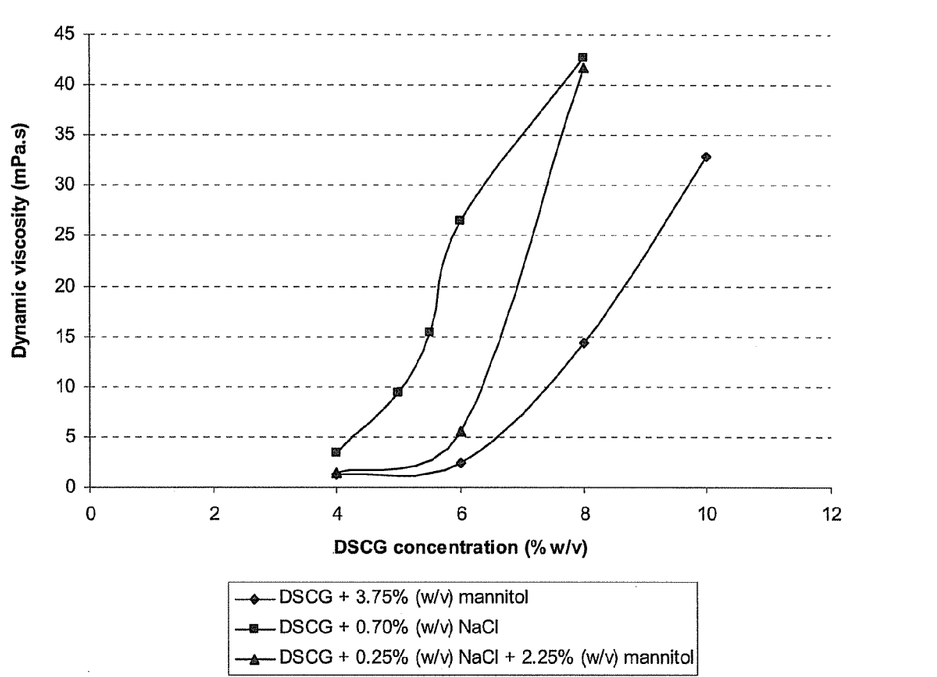
FIG. 1 shows the dynamic viscosity of differently concentrated DSCG solutions, not isotonised, isotonised with sodium chloride or isotonised with a mixture of sodium chloride and mannitol.

FIG. 1 further illustrates that the dynamic viscosity of DSCG solutions increases strongly upon increasing the DSCG concentration. The addition of an ionic tonicity-adjusting agent (sodium chloride) increases the dynamic viscosity even stronger. Replacing part of the ionic tonicity-adjusting agent by a non-ionic tonicity-adjusting agent, such that the molar ratio of non-ionic to ionic tonicity-adjusting agent is 2.88, allows formulating highly concentrated DSCG solutions with an acceptable dynamic viscosity. This is especially clear for DSCG concentrations below 8% (w/v): when NaCl is replaced by a mixture of mannitol and NaCl as isotonising agent for a 6% (w/v) DSCG solution, the viscosity decreases from 26.45 to 5.53 mPa·s, respectively.

TABLE 2

Dynamic viscosity of formulations with different concentrations of DSCG, sodium chloride and/or mannitol

| No. | DSCG conc. (% w/v) | Mannitol Conc. (% w/v) | Mannitol Conc. (mol/l) | NaCl Conc. (% w/v) | NaCl Conc. (mol/l) | Dyn. viscosity (mPa · s) |
|---|---|---|---|---|---|---|
| 1* | 4.00 | 3.75 | 0.206 | — | — | 1.34 |
| 2* | 6.00 | 3.75 | 0.206 | — | — | 2.41 |
| 3* | 8.00 | 3.75 | 0.206 | — | — | 14.34 |
| 4* | 10.00 | 3.75 | 0.206 | — | — | 32.85 |
| 5* | 4.00 | — | — | 0.70 | 0.120 | 3.48 |
| 6* | 5.00 | — | — | 0.70 | 0.120 | 9.40 |
| 7* | 5.50 | — | — | 0.70 | 0.120 | 15.40 |
| 8* | 6.00 | — | — | 0.70 | 0.120 | 26.45 |
| 9* | 8.00 | — | — | 0.70 | 0.120 | 42.67 |
| 10 | 4.00 | 2.25 | 0.124 | 0.25 | 0.043 | 1.36 |
| 11 | 6.00 | 2.25 | 0.124 | 0.25 | 0.043 | 5.53 |
| 12 | 8.00 | 2.25 | 0.124 | 0.25 | 0.043 | 41.68 |

*for comparison

Example 3

In this example, the influence of another sodium salt on the viscosity of a DSCG solution is demonstrated. A first solution was prepared containing 6.0% (w/v) DSCG with 2.95% (w/v) (or 0.135 mol/l) sodium gluconate in water for injection. A second solution was prepared containing 5% (w/v) DSCG with 2.65% (w/v) mannitol (0.145 mol/l) and 1.0% (w/v) (or 0.046 mol/l) sodium gluconate in water for injection. The molar ratio of the non-ionic tonicity-adjusting excipient to the ionic tonicity-adjusting excipient is 3.17. Surprisingly, the viscosity of the solution only containing sodium gluconate was much higher than the viscosity of the solution with a mixture of ionic and non-ionic isotonising agent, being 53.41 mPa·s and 2.50 mPa·s, respectively.

Example 4

In another experiment, another alkali metal salt is used. Similar as in Example 3, a 6.0% (w/v) DSCG solution isotonised with potassium chloride or isotonised with a mixture of mannitol and potassium chloride was prepared. The first solution comprised 6.0% (w/v) DSCG and 1.15% (w/v) (or 0.154 mol/l) potassium chloride, whereas the second solution comprised 6.0% (w/v) DSCG, 2.25% (w/v) mannitol (0.124 mol/l), and 0.319% (w/v) (or 0.043 mol/l) potassium chloride. The molar ratio of the non-ionic tonicity-adjusting excipient to the ionic tonicity-adjusting excipient is 2.89. Similar to the previous unexpected findings, the viscosity of the first solution was much higher compared with the viscosity of the second solution utilizing an excipient mixture of a salt and a non-ionic excipient (22.65 mPa·s versus 3.81 mPa·s).

Example 5

The tolerability after inhalation of a 6% (w/v) DSCG solution containing 3.75% (w/v) mannitol (Formulation 2 from Example 2), was compared with a 6% (w/v) DSCG solution containing 2.25% (w/v) mannitol and 0.25% (w/v) sodium chloride (Formulation 11 from Example 2; molar ratio 2.89). The osmolality of the solutions was 300 mOsm/kg and 288 mOsm/kg, respectively, i.e. the osmolality was close to the osmolality of physiological fluids (290 mOsm/kg). For both inhalation sessions, 1 ml of the solution was filled in the reservoir of a PARI eFlow vibrating membrane nebulizer and inhaled by volunteers. It was found that the solution without sodium chloride was more irritating upon inhalation than the solution where an excipient mix consisting of mannitol and sodium chloride was used. This was unexpected, since the solutions had a similar osmolality.

Example 6

In another example, different non-ionic tonicity-adjusting excipients for isotonisation of DSCG solutions (DSCG concentration: 6% w/v) are compared with respect to their influence on the dynamic viscosity. For comparison, a solution isotonised with sodium chloride was also prepared. The solutions were prepared by weighing the compounds and dissolving them in water for injection. Afterwards, the solutions were sterile filtered and filled in polystyrene vials. The solutions were stored at 5° C., 25° C. and 40° C. None of the compositions showed visual instability. All formulations are chemically stable during a storage period of 3 months.

TABLE 3

Composition, osmolality and dynamic viscosity of highly concentrated (6% w/v) DSCG solutions isotonised with sodium chloride and different non-ionic tonicity-adjusting agents

| No | Type | Non-ionic excipient Conc. (% w/v) | Non-ionic excipient Conc. (mol/l) | NaCl Conc. (% w/v) | NaCl Conc. (mol/l) | Molar ratio | Osmolality (mOsm/kg) | Dyn. visc. (mPa · s) |
|---|---|---|---|---|---|---|---|---|
| 1 | — | — | — | 0.65 | 0.111 | — | 279 | 26.45 |
| 2 | Mannitol | 2.25 | 0.124 | 0.25 | 0.043 | 2.89 | 288 | 5.53 |

TABLE 3-continued

Composition, osmolality and dynamic viscosity of highly concentrated (6% w/v) DSCG solutions isotonised with sodium chloride and different non-ionic tonicity-adjusting agents

| | | Non-ionic excipient | | NaCl | | | | |
|---|---|---|---|---|---|---|---|---|
| No | Type | Conc. (% w/v) | Conc. (mol/l) | Conc. (% w/v) | Conc. (mol/l) | Molar ratio | Osmolality (mOsm/kg) | Dyn. visc. (mPa · s) |
| 3 | Xylitol | 2.00 | 0.131 | 0.25 | 0.043 | 3.07 | 297 | 5.14 |
| 4 | Sorbitol | 2.25 | 0.124 | 0.25 | 0.043 | 2.89 | 285 | 5.15 |
| 5 | Lactose | 4.46 | 0.124 | 0.25 | 0.043 | 2.89 | 304 | 5.36 |
| 6 | Trehalose | 4.70 | 0.124 | 0.25 | 0.043 | 2.90 | 298 | 5.37 |

The composition of the solutions and their osmolality and dynamic viscosity is shown in Table 3. Surprisingly, the DSCG solution isotonised with sodium chloride, showed an about five-fold higher viscosity compared with the solutions isotonised with a mixture of sugar alcohols or sugars and sodium chloride.

Example 7

A formulation containing 5% (w/v) DSCG, 2.21% (w/v) (i.e. 0.145 mol/l) xylitol, and 1% (w/v) (i.e. 0.091 mol/l) sodium pyruvate was prepared (molar ratio: 1.6). The solution was sterile filtered and filled in sterile polystyrene vials for storage at 5° C., 25° C. and 40° C. The dynamic viscosity measured immediately after preparation was 2.20 mPa·s. The solution was well tolerated by a volunteer upon inhalation with an eFlow nebulizer and did not cause any irritation or taste sensitisation.

Example 8

In a further experiment, the effect of a complexing agent was evaluated. The composition of the formulations is given in Table 4. The dynamic viscosity of the DSCG solutions was measured immediately after preparation and results are shown in Table 4.

TABLE 4

Composition and dynamic viscosity of differently concentrated DSCG solutions containing different isotonising agents, all or not combined with additional excipients.

| No. | DSCG conc. (% w/v) | Mannitol conc. (% w/v) | NaCl conc. (% w/v) | Molar ratio | NaEDTA conc. (% w/v) | Dynamic viscosity (mPa · s) |
|---|---|---|---|---|---|---|
| 1 | 6.00 | 2.25 | 0.25 | 2.89 | — | 5.53 |
| 2 | 6.00 | 2.25 | 0.25 | 2.89 | 0.02 | 5.78 |

Example 9

The use of propylene glycol as non-ionic tonicity-adjusting excipient is demonstrated. A solution containing 4% (w/v) DSCG, 1.46% (w/v) propylene glycol, 0.225% (w/v) sodium chloride, and 0.25% (w/v) sodium citrate (molar ratio: 4.08) was prepared. The osmolality of the solution was 375 mOsm/kg and the dynamic viscosity was 1.28 mPa·s.

Example 10

The aerosol characteristics of a 6% (w/v) DSCG formulation nebulized with a PARI LC® SPRINT Junior jet nebulizer, a customized eFlow 30S and a customized investigational eFlow Closed System (CS) were investigated. The formulation contained 2.25% (w/v) mannitol and 0.25% (w/v) NaCl (molar ratio: 2.89). The nebulized volume was 2 ml (containing 120 mg DSCG) for the jet nebulizer and 0.75 ml (containing 45 mg DSCG) for both vibrating membrane nebulizers. The aerodynamic size distribution was assessed with a Next Generation Impactor (NGI) operated at a flow rate of 15 L/min. The NGI was cooled to 18° C.±0.5° C. to avoid evaporation of the droplets. The inspiratory air was conditioned to 23° C.±2° C. and 50%±5% relative humidity (RH) or to 23° C.±2° C. and 95%±5% RH. The test was performed in triplicate for each nebulizer. The amount of DSCG on the different stages of the impactor was quantified by a validated HPLC method. The Fine Particle Dose (FPD)≤5 µm, FPD≤3.3 µm, the mass median aerodynamic diameter (MMAD), and geometric droplet size distribution (GSD) were calculated using the Copley C.I.T.D.A.S. Vers 2.00 software. The FPD was obtained in mg. The results are shown in Table 5.

TABLE 5

Humidity effects on average FPD, MMAD, and GSD in an NGI when nebulizing 2 ml and 0.75 ml of a 6% DSCG solution with a PARI LC ® SPRINT Junior nebulizer and two eFlow nebulizer configurations, respectively (n = 3)

| | Nebulizer | | | | | |
|---|---|---|---|---|---|---|
| | PARI LC ® SPRINT Junior | | eFlow 30S | | Investigational eFlow CS | |
| | Loaded dose/volume | | | | | |
| | 120 mg/2 ml | | 45 mg/0.75 ml | | 45 mg/0.75 ml | |
| RH (%) | 50 | 95 | 50 | 95 | 50 | 95 |
| FPD ≤ 5 µm (mg) | n.p.* | 36.6 | 36.1 | 33.6 | 29.8 | 32.7 |
| FPD ≤ 3.3 µm (mg) | n.p.* | 25.7 | 24.5 | 19.1 | 21.9 | 20.7 |
| MMAD (µm) | n.p.* | 3.5 | 3.0 | 3.5 | 2.8 | 3.2 |
| GSD | n.p.* | 2.14 | 1.51 | 1.55 | 1.53 | 1.57 |

*n.p. = nebulization not possible

Surprisingly, the 6% DSCG solution could not be nebulized at 50% relative humidity with the PARI LC Sprint Junior jet nebulizer in this experimental setting. This effect was most probably related to evaporation of the liquid in the medication cup of the nebulizer causing an unexpected viscosity increase during nebulization. As already shown in previous examples, DSCG formulations exhibit a high susceptibility for a viscosity increase. It is generally known that the viscosity of formulations increases when temperature decreases. As evaporation of a liquid, as occurs in the reservoir of a jet nebulizer, causes a temperature decline and an increase of concentration of the compounds, it might be expected that both factors will have contributed to a dramatic increase of viscosity. Since no evaporation of liquid occurs in the medication cup of eFlow nebulizers, nebulization of highly concentrated DSCG solutions is not hampered nor negatively affected as in jet nebulizers. Results at two different environmental conditions showed that the fine particle dose below 3.3 µm of the eFlow CS nebulizer seems to be less affected by relative humidity than with the eFlow 30S nebulizer.

Example 11

Similar as described in Example 10, the NGI was used to evaluate the difference when nebulizing a 1% (w/v) DSCG solution (isotonised with NaCl) and a 6% (w/v) DSCG solution (isotonised with 0.25% (w/v) NaCl and 2.25% (w/v) mannitol) with a PARI LC® SPRINT Junior jet nebulizer and an eFlow 30S vibrating membrane nebulizer. The results for nebulising with the inspiratory air conditioned to 23° C.±2° C. and 50%±5% RH are shown in Table 6, whereas the results for nebulisation with the inspiratory air conditioned to 23° C.±2° C. and 95%±5% RH are shown in Table 7.

nebulizer is used. Despite the fact the label claim was only 2.25-fold higher for the inventive formulation, the fine particle dose smaller than 3.3 µm was at 50% RH 2.6-fold and at 95% RH 2.5-fold higher when the inventive formulation was nebulized via an eFlow 30S. As a consequence, the MMAD was also reduced. These results are most important for a therapeutic effect, since chymase-positive mast cells being crucial for the inflammation process in the lungs and triggering asthma are located in the lung periphery, such as the alveolar attachments (Balzer et al. Mast cells in severe asthma. Am. J. Resp. and Crit Care Med. 2005; 171: 431-439). These unexpected in-vitro data when nebulizing the inventive formulation with a customized eFlow 30S nebulizer offer new and better therapeutic treatment options over current established delivery concepts shown for a 1% DSCG solution in the PARI LC® Sprint Junior jet nebulizer.

The more efficient and higher dosage delivery when combining the inventive formulation with an electronic nebulizer may also allow reducing the dosing frequency compared to currently approved treatment regimes. Thus a 3-4 times daily administration of DSCG 1% via jet nebulizers can potentially be reduced to once or twice daily when using the inventive DSCG formulation with an electronic nebulizer. Due to the much higher delivery efficiency smaller volumes (0.5-1 ml) will be feasible which can be inhaled in less than 3 min

TABLE 6

Comparison of the FPD, MMAD and GSD measured in an NGI with inspiratory air RH of 50% when nebulizing 1% and 6% (w/v) DSCG solutions with a PARI LC ® SPRINT Junior nebulizer and an eFlow nebulizer (n = 3)

| Nebulizer | PARI LC ® SPRINT Junior | | eFlow 30S | |
|---|---|---|---|---|
| Loaded dose/volume | 20 mg/2 ml | 120 mg/2 ml | 20 mg/2 ml | 45 mg/0.75 ml |
| Concentration | 1% (w/v) | 6% (w/v) | 1% (w/v) | 6% (w/v) |
| FPD ≤ 5 µm (mg) | 6.7 | n.p.* | 15.6 | 36.1 |
| FPD ≤ 3.3 µm (mg) | 4.4 | n.p.* | 9.4 | 24.5 |
| MMAD (µm) | 3.8 | n.p.* | 3.3 | 3.0 |
| GSD | 2.0 | n.p.* | 1.5 | 1.5 |

*n.p. = nebulization not possible

TABLE 7

Comparison of the FPD, MMAD and GSD measured in an NGI with inspiratory air RH of 95% when nebulizing 1% and 6% (w/v) DSCG solutions with a PARI LC ® SPRINT Junior nebulizer and an eFlow nebulizer (n = 3)

| Nebulizer | PARI LC ® SPRINT Junior | | eFlow 30S | |
|---|---|---|---|---|
| Loaded dose/volume | 20 mg/2 ml | 120 mg/2 ml | 20 mg/2 ml | 45 mg/0.75 ml |
| Concentration | 1% (w/v) | 6% (w/v) | 1% (w/v) | 6% (w/v) |
| FPD ≤ 5 µm (mg) | 7.4 | 36.6 | 14.7 | 33.6 |
| FPD ≤ 3.3 µm (mg) | 4.8 | 25.7 | 7.6 | 19.1 |
| MMAD (µm) | 3.8 | 3.5 | 3.6 | 3.5 |
| GSD | 2.1 | 2.1 | 1.5 | 1.6 |

Data from Table 6 and 7 indicate that the nebulization of the inventive formulation delivers a higher fine particle dose smaller than 3.3 µm when a customized electronic eFlow 30S providing at the same time a lung dose which may be several fold. These aspects will improve drug adherence of the inhaled therapy known to strongly correlate with inhalation time and administration frequency. These aspects are particularly important with respect to the inhaled drug therapy in children and adolescents.

Example 12

Nebulization efficiency of Formulation 2 described in Example 6 (i.e. 6% (w/v) DSCG with 0.25% (w/v) NaCl and 2.25% (w/v) mannitol) was also evaluated applying breath simulation tests. Breath simulation experiments were performed using a COMPAST™ breath simulator (PARI GmbH, Starnberg, Germany). The solutions were nebulized with a PARI eFlow 30S vibrating membrane nebulizer and a PARI investigational eFlow Closed System (CS) vibrating membrane nebulizer, applying breathing patterns representative for a 3-year old child (tidal volume: 125 ml/breaths per minute: 24/inspiration to expiration ratio: 40:60) and a 10-year old child (tidal volume: 225 ml/breaths per minute: 16/inspiration to expiration ratio: 40:60). Tests were conducted with three devices of each nebulizer in duplicate. The devices were filled with 0.75 ml of the 6% inventive DSCG solution and connected to the breath simulator. The amount of DSCG in the samples collected from inspiratory filters corresponding to the emitted dose ex-mouthpiece was quantified by a validated HPLC-method. This set-up allowed measuring the delivered dose (DD), the nebulization time, the drug delivery rate (DDR) and allowed calculating with reference to aerodynamic data regarding the droplet size the respirable dose (RD) and respirable drug delivery rate (RDDR). Hence, data allow conclusion to which extent nebulization efficiency of the inventive 6% DSCG solution will be affected when breathing patterns representative for children of 3 and 10 years are mimicked. Results of these breath simulation tests are shown in Table 8.

TABLE 8

DD, RD, nebulization time, DDR and RDDR (average) when nebulizing 0.75 ml of a 6% DSCG solution with two different eFlow configurations using breathing patterns representative for children of 3 and 10 years old (n = 6)

| | Nebulizer | | | |
|---|---|---|---|---|
| | eFlow 30S | | Investigational eFlow CS | |
| | Breathing pattern | | | |
| | 3 year old child | 10 year old child | 3 year old child | 10 year old child |
| DD (mg) | 28.6 | 26.5 | 30.2 | 30.6 |
| DD (%) | 61.2 | 55.7 | 64.4 | 65.4 |

TABLE 8-continued

DD, RD, nebulization time, DDR and RDDR (average) when nebulizing 0.75 ml of a 6% DSCG solution with two different eFlow configurations using breathing patterns representative for children of 3 and 10 years old (n = 6)

| | Nebulizer | | | |
|---|---|---|---|---|
| | eFlow 30S | | Investigational eFlow CS | |
| | Breathing pattern | | | |
| | 3 year old child | 10 year old child | 3 year old child | 10 year old child |
| Nebulization time (min) | 2.4 | 2.4 | 2.7 | 2.6 |
| RD < 5 μm (mg) | 25.3 | 23.4 | 26.9 | 27.2 |
| RD < 5 μm (%) | 54.1 | 49.2 | 57.4 | 58.2 |
| RD < 3.3 μm (mg) | 17.2 | 15.9 | 19.7 | 20.0 |
| RD < 3.3 μm (%) | 36.8 | 33.5 | 42.1 | 42.6 |
| DDR (%/min) | 26.1 | 23.1 | 24.7 | 25.2 |
| RDDR (% <5 μm/min) | 23.1 | 20.5 | 22.0 | 22.4 |

Results show no striking differences with respect to the tested parameters when comparing the two nebulizers. However, the investigational eFlow CS seems to be less affected by the breathing pattern as the eFlow 30S.

Example 13

Further formulations were prepared with different DSCG concentrations and different concentration ratios of non-ionic tonicity adjusting agents to ionic tonicity adjusting agents. The solutions were prepared by weighing the compounds described in Table 9 and Table 10 and dissolving them in water for injection. The dynamic viscosity, shown in Table 9 and 10 for the respective formulations, is in all cases considerably higher for formulations where the molar ratio of non-ionic tonicity adjusting agent to ionic tonicity adjusting agent is smaller than 1, despite the mass ratio being larger than 1. This shows that the molar ratio, rather than the mass ratio, is relevant for obtaining highly concentrated DSCG solutions with an acceptable viscosity.

TABLE 9

Composition and dynamic viscosity of differently concentrated DSCG solutions with mannitol and NaCl as isotonising agents used in different concentration ratios

| | | Mannitol | | NaCl | | | | |
|---|---|---|---|---|---|---|---|---|
| No | DSCG conc. (% w/v) | Conc. (% w/v) | Conc. (mol/l) | Conc. (% w/v) | Conc. (mol/l) | Mass ratio | Molar ratio | Dyn. visc. (mPa · s) |
| 1 | 4 | 2.70 | 0.148 | 0.30 | 0.051 | 9.0 | 2.9 | 1.35 |
| 2 | 4 | 1.20 | 0.066 | 0.55 | 0.094 | 2.2 | 0.7 | 2.10 |
| 3 | 5 | 2.50 | 0.137 | 0.30 | 0.051 | 8.3 | 2.7 | 2.17 |
| 4 | 5 | 1.00 | 0.055 | 0.55 | 0.094 | 1.8 | 0.6 | 6.35 |

TABLE 9-continued

Composition and dynamic viscosity of differently concentrated DSCG solutions with mannitol and NaCl as isotonising agents used in different concentration ratios

| No | DSCG conc. (% w/v) | Mannitol | | NaCl | | Mass ratio | Molar ratio | Dyn. visc. (mPa · s) |
|---|---|---|---|---|---|---|---|---|
| | | Conc. (% w/v) | Conc. (mol/l) | Conc. (% w/v) | Conc. (mol/l) | | | |
| 5 | 6 | 2.10 | 0.115 | 0.30 | 0.051 | 7.0 | 2.2 | 6.43 |
| 6 | 6 | 0.70 | 0.038 | 0.55 | 0.094 | 1.3 | 0.4 | 16.75 |

TABLE 10

Composition and dynamic viscosity of 5% (w/v) DSCG solutions with xylitol and NaCl as isotonising agents used in different concentration ratios

| No | DSCG conc. (% w/v) | Xylitol | | NaCl | | Mass ratio | Molar ratio | Dyn. visc. (mPa · s) |
|---|---|---|---|---|---|---|---|---|
| | | Conc. (% w/v) | Conc. (mol/l) | Conc. (% w/v) | Conc. (mol/l) | | | |
| 1 | 5 | 2.50 | 0.164 | 0.30 | 0.051 | 8.3 | 3.2 | 2.19 |
| 2 | 5 | 1.00 | 0.066 | 0.55 | 0.094 | 1.8 | 0.7 | 6.04 |

What is claimed is:

1. A liquid aqueous pharmaceutical solution comprising from 2 to 10% (w/v) of disodium cromoglycate and a tonicity-adjusting component, wherein
   (i) the tonicity-adjusting component is a combination of at least one non-ionic tonicity-adjusting excipient and at least one ionic tonicity-adjusting excipient,
   (ii) the concentration of the ionic tonicity-adjusting excipient(s) is not more than about 0.1 mol/l, and
   (iii) the molar ratio of the non-ionic tonicity-adjusting excipient(s) to the ionic tonicity-adjusting excipient(s) is at least 1:1.

2. The pharmaceutical solution according to claim 1, wherein the molar ratio of the non-ionic tonicity-adjusting excipient(s) to the ionic tonicity-adjusting excipient(s) is selected to effect a dynamic viscosity of the solution of less than about 10 mPa·s.

3. The pharmaceutical solution according to claim 1, wherein the concentration of the non-ionic tonicity-adjusting excipient(s) is at least about 0.03 mol/l.

4. The pharmaceutical solution according to claim 1, wherein the concentration of the tonicity-adjusting component is selected to effect an osmolality from about 200 to about 1200 mOsm/kg.

5. The pharmaceutical solution according to claim 1, wherein the concentration of disodium cromoglycate is from about 4% to about 8% (w/v).

6. The pharmaceutical solution according to claim 1, wherein the concentration of disodium cromoglycate is from about 4% to about 6.5% (w/v).

7. The pharmaceutical solution according to claim 1, wherein the non-ionic tonicity-adjusting excipient is a carbohydrate or a sugar alcohol.

8. The pharmaceutical solution according to claim 1, wherein the ionic tonicity-adjusting excipient is an alkali metal salt.

9. The pharmaceutical solution according to claim 1, further comprising an antioxidant.

10. The pharmaceutical solution according to claim 1 for use as a medicament.

11. The pharmaceutical solution according to claim 1 for use as a medicament for the treatment of asthma and other respiratory diseases involving inflammation and/or infection.

12. The pharmaceutical solution according to claim 1 for use as a medicament for once- or twice-daily administration.

13. The pharmaceutical solution according to claim 1 for use as a medicament for administration in the form of an inhalable aerosol.

14. A method of generating an aerosol comprising aerosolizing an aqueous pharmaceutical solution of claim 1 by means of a perforated membrane type nebuliser, wherein
   (a) a nominal dose of at least 40 mg of disodium cromoglycate is aerosolised within less than 3 minutes;
   (b) an actually delivered dose via a mouthpiece of the nebuliser is more than 50% of the nominal dose of disodium cromoglycate;
   (c) a fraction of disodium cromoglycate which is delivered as fine particles having a diameter below 3.3 µm is more than 30% of the nominal dose; and
   (d) a volume of the solution comprising a single unit dose is not more than 1.5 ml.

15. The pharmaceutical solution according to claim 1, wherein the non-ionic tonicity-adjusting excipient is selected from glucose, lactose, sucrose, trehalose, mannitol, xylitol, sorbitol, and mixtures thereof.

16. The pharmaceutical solution according to claim 1, wherein the ionic tonicity-adjusting excipient is selected from sodium chloride, sodium gluconate, sodium pyruvate, potassium chloride, and mixtures thereof.

17. The pharmaceutical solution according to claim 9, wherein the antioxidant is selected from sodium gluconate, sodium pyruvate, sodium EDTA and mixtures thereof.

18. The pharmaceutical solution according to claim 13, wherein the aerosol is generated by a perforated membrane type nebuliser.

* * * * *